United States Patent
Kuehl et al.

(10) Patent No.: US 11,571,318 B1
(45) Date of Patent: Feb. 7, 2023

(54) ANKLE BRACE

(71) Applicant: MUELLER SPORTS MEDICINE, INC., Prairie du Sac, WI (US)

(72) Inventors: Sarah Kuehl, Madison, WI (US); Kayla Daken, Prairie du Sac, WI (US)

(73) Assignee: MUELLER SPORTS MEDICINE, INC., Prairie du Sac, WI (US)

( * ) Notice: Subject to any disclaimer, the term of this patent is extended or adjusted under 35 U.S.C. 154(b) by 254 days.

(21) Appl. No.: 16/442,121

(22) Filed: Jun. 14, 2019

(51) Int. Cl.
*A61F 5/01* (2006.01)

(52) U.S. Cl.
CPC .................. *A61F 5/0111* (2013.01)

(58) Field of Classification Search
CPC ............ A61F 5/01–0104; A61F 5/0111; A61F 5/0113; A61F 5/0127; A61F 5/0195; A61F 13/06; A61F 13/064–069; A43B 23/26; A43B 7/00; A43B 7/14; A43B 7/18–20
USPC .......................................................... 36/1.5
See application file for complete search history.

(56) References Cited

U.S. PATENT DOCUMENTS

| | | | | |
|---|---|---|---|---|
| 1,731,276 A * | 10/1929 | Skoglund | ............ | A61F 13/066 602/62 |
| 3,298,365 A * | 1/1967 | Lewis | ................... | A61F 5/0111 602/27 |
| 3,308,829 A * | 3/1967 | Edwards | .................. | A43B 7/00 36/142 |
| 3,327,410 A * | 6/1967 | Park, Sr. | .................. | A43B 5/00 36/89 |
| 4,313,433 A * | 2/1982 | Cramer | ................. | A61F 13/066 602/27 |
| 5,067,486 A * | 11/1991 | Hely | ...................... | A61F 13/066 602/27 |
| 5,069,202 A * | 12/1991 | Prock | .................... | A61F 5/0127 602/27 |
| 5,921,947 A * | 7/1999 | Kessler | ................... | A61F 13/64 602/27 |
| 6,663,583 B1 * | 12/2003 | Janis | ..................... | A61F 5/0111 602/65 |
| 2012/0029404 A1 * | 2/2012 | Weaver, II | ............ | A61F 5/0111 602/27 |
| 2016/0106183 A1 * | 4/2016 | Roberson | ............. | A43B 1/0027 36/136 |

* cited by examiner

*Primary Examiner* — Michelle J Lee
(74) *Attorney, Agent, or Firm* — Rick L. Abegglen (57) ABSTRACT

An ankle brace with a base having an inelastic body portion extending from an ankle opening to a forefoot opening, with a continuous elastic band sewn to the forefoot opening, and a floating tongue bearing a band loop. The floating tongue is not sewn to the inelastic body portion of the base, instead the floating tongue is sewn only to the elastic band at a single point underneath the band loop.

26 Claims, 8 Drawing Sheets

ANKLE BRACE

FIELD OF THE INVENTION

This invention relates generally to the field of supports for the human body. More particularly, the present invention relates to an improved ankle brace that improves conformance to the foot and reduces bunching at the front of the brace, resulting in enhanced comfort and performance compared to the prior art.

BACKGROUND OF THE INVENTION

Athletes have used ankle braces for many years. One particular ankle brace is U.S. Pat. No. 5,067,486 for "Ankle Stabilizing Appliance". One practical problem with ankle braces, including but not limited to those of the sort taught in U.S. Pat. No. 5,067,486, is bunching or ripples of fabric in the tongue and lace area (see e.g. bunching and rippling of the tongue 28 shown in FIGS. 2 and 4 in U.S. Pat. No. 5,067,486). When the laces on the brace are tightened, this bunching or rippling can produce localized ridges of pressure that can feel uncomfortable to the wearer, and make it harder to apply the brace with uniform compression across the entire foot and ankle area.

What is needed is an improved ankle brace that avoids or reduces these problems and provides superior support compared to the prior art.

SUMMARY OF THE INVENTION

A first embodiment of the invention is an ankle brace having a base comprising an inelastic body portion having a forefoot opening and a 360-degree elastic forefoot band sewn to the forefoot opening, wherein the elastic forefoot band encircles the entire forefoot, with a closure system (e.g. shoelaces, cords, or straps bearing hook-and-loop fasteners) for tightening the inelastic body portion about the foot and ankle, along with a floating tongue with a band loop, where the floating tongue is not sewn to the inelastic body portion. The floating tongue is preferably sewn only to the elastic forefoot band at a single location, whereby the edges of the tongue can slide under the inelastic body portion to reduce bunching when the base is tightened about the foot and ankle.

In a preferred embodiment, the elastic forefoot band is about 1" wide (between 0.75" and 1.5" wide), the floating tongue includes a band loop, the elastic forefoot band extends through the band loop, and the elastic forefoot band is sewn to the floating tongue at a single point inside the band loop. Alternatively, if the elastic forefoot band is not sewn to the floating tongue, then the elastic forefoot band may extend slidably through the band loop. The floating tongue preferably also includes a laces loop, and at least a portion of the shoelaces may extend slidably through the laces loop.

A second embodiment of the invention is an ankle brace having a base comprising an inelastic body portion having a forefoot opening and a 360-degree elastic forefoot band sewn to the forefoot opening, a closure system, a pair of support straps, and a finishing wrap, wherein the elastic forefoot band encircles the entire forefoot, along with a floating tongue, where the floating tongue is sewn only to the elastic forefoot band.

Further objects, features, and advantages of the invention will be apparent from the following detailed description when taken in conjunction with the accompanying drawings.

DETAILED DESCRIPTION OF THE INVENTION

An ankle brace 10 according to the invention has a base 11 that includes a body portion 12 extending from an ankle end to a toe end, and an elastic band 13 that extends 360-degrees around the forefoot area, sewn to the edges of the body portion 12 at the forefoot or toe end. The body portion 12 may be formed of a thin and lightweight, yet sturdy and inelastic, sheet material shaped to conform closely to the human foot and ankle.

The elastic band 13 is preferably formed as a continuous seamless loop of woven, knit, or nonwoven material that encircles the forefoot without any stitches or other discontinuities so the loop is smooth and stretches uniformly to avoid potential discomfort of a seam. The elastic band 13 could be made of a circular knitted material, or ultrasonic welding or heat sealing could be used to avoid a seam. Alternatively, if a seam is used, it is preferably placed under the band loop of the tongue.

Although stitches 19 are a preferred method of permanently fastening together various components of the ankle brace 10, this is not required and other permanent fastening methods could be used such as glue or ultrasonic welding, heat welding, rivets, or other methods. As used in this application and its claims, the term "sewn" means permanently fastened together by any such means, including but not limited to permanently fastened together with stitches or sewing.

The elastic band 13 is preferably between 0.75"-1.5" wide, and in a preferred embodiment is 1.0" wide. The material of the elastic band 13 is preferably elastic with high resilience and limited stretch in a lengthwise direction (around the loop). The elastic band 13 may be elastic in a side-to-side direction (across the width of the band 13), but this is not required and in a preferred embodiment the elastic band 13 is substantially inelastic in a side-to-side direction. The material of the elastic band 13 may comprise, for example, cotton, polyester, nylon, spandex, and/or any combination thereof.

Figure 4:
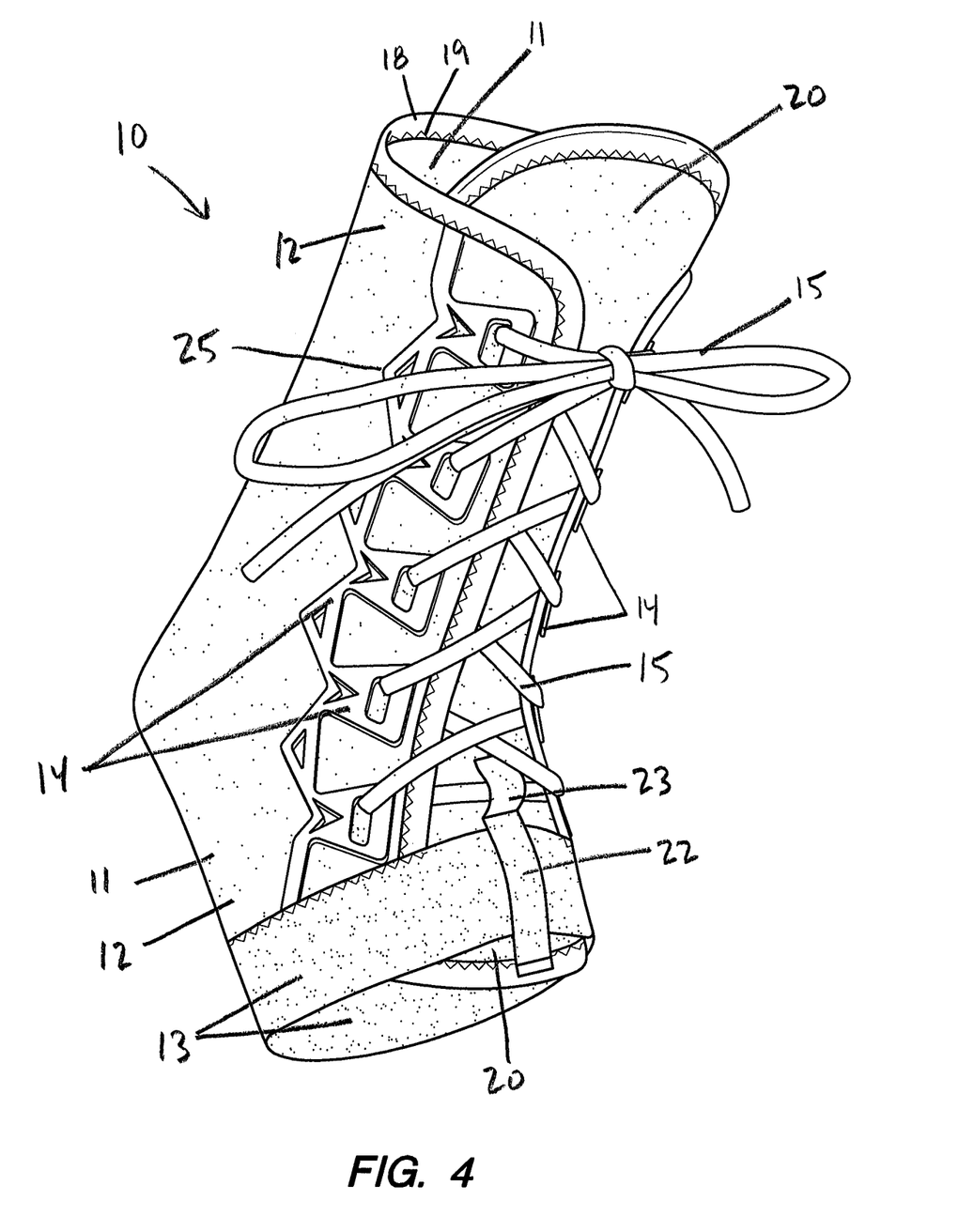
FIG. 4 is a front left perspective view of the ankle brace of FIG. 1, with laces applied but with the finishing wrap, the support strap, and the support strap mounting patches removed.

The ankle brace 10 has a closure system, for example comprising forward edges bearing eyelet strips 14, and (as shown in FIG. 4) laces for tightening the ankle brace 10 about the foot and ankle of a person. The ankle brace 10 has a heel opening 16, and an achilles elastic panel 17 above the heel opening. Various components of the brace 10, such as the body portion 12 of the base 11, may have edging 18 secured with stitches 19.

Figure 1:
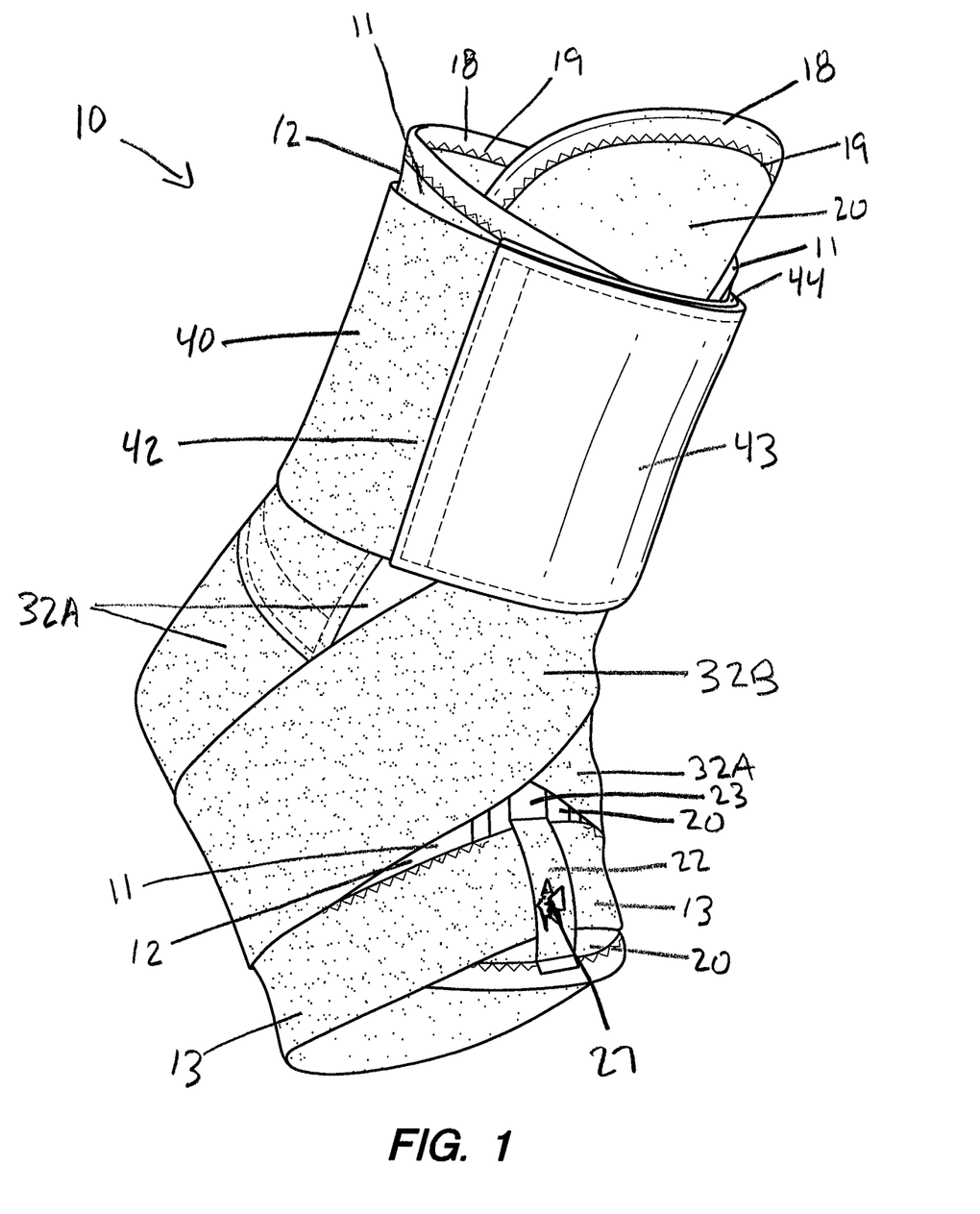
FIG. 1 depicts a front left perspective view of an ankle brace according to the invention as normally applied to the foot and ankle of a person.
Figure 2:
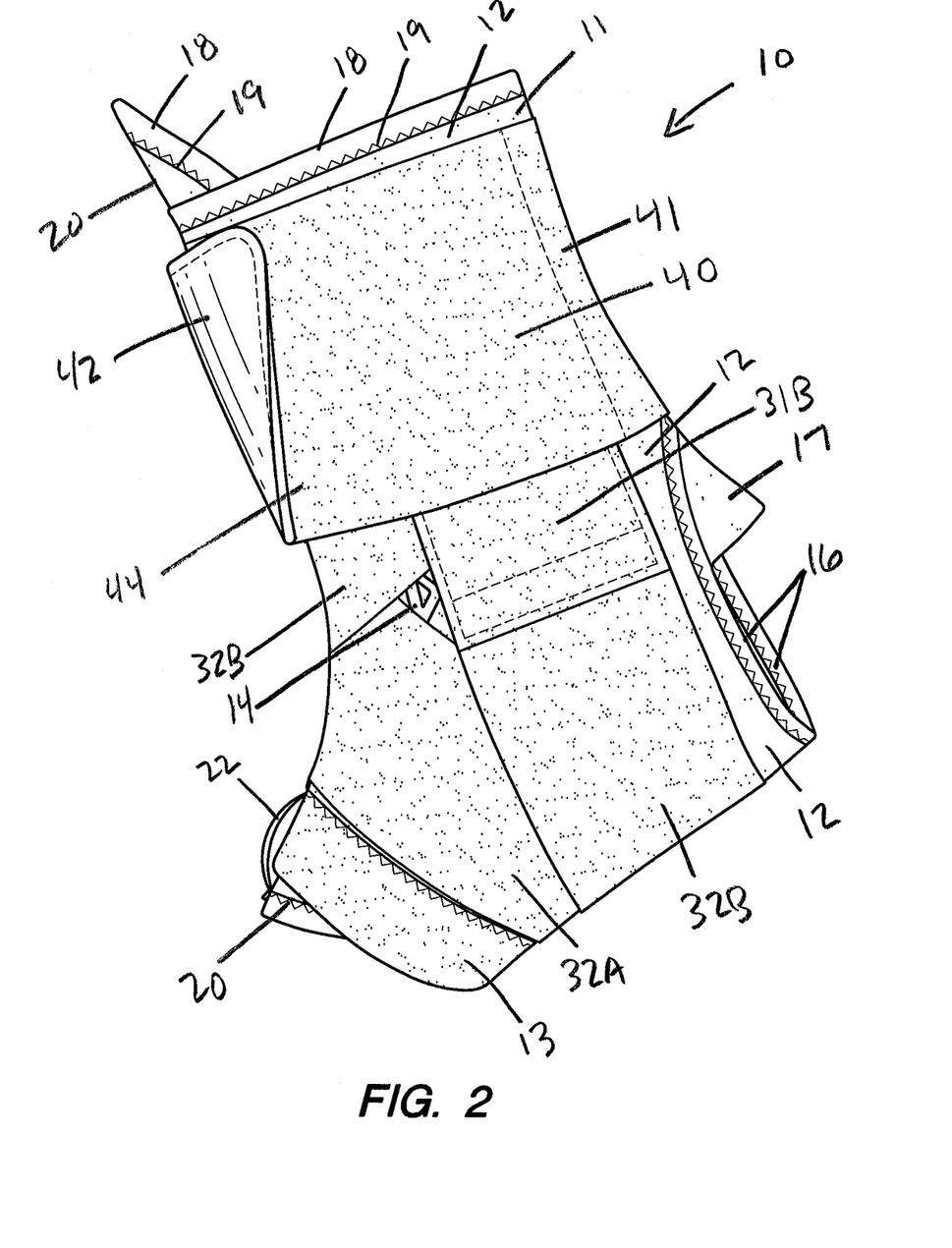
FIG. 2 is a right side view of the ankle brace of FIG. 1.
Figure 3:
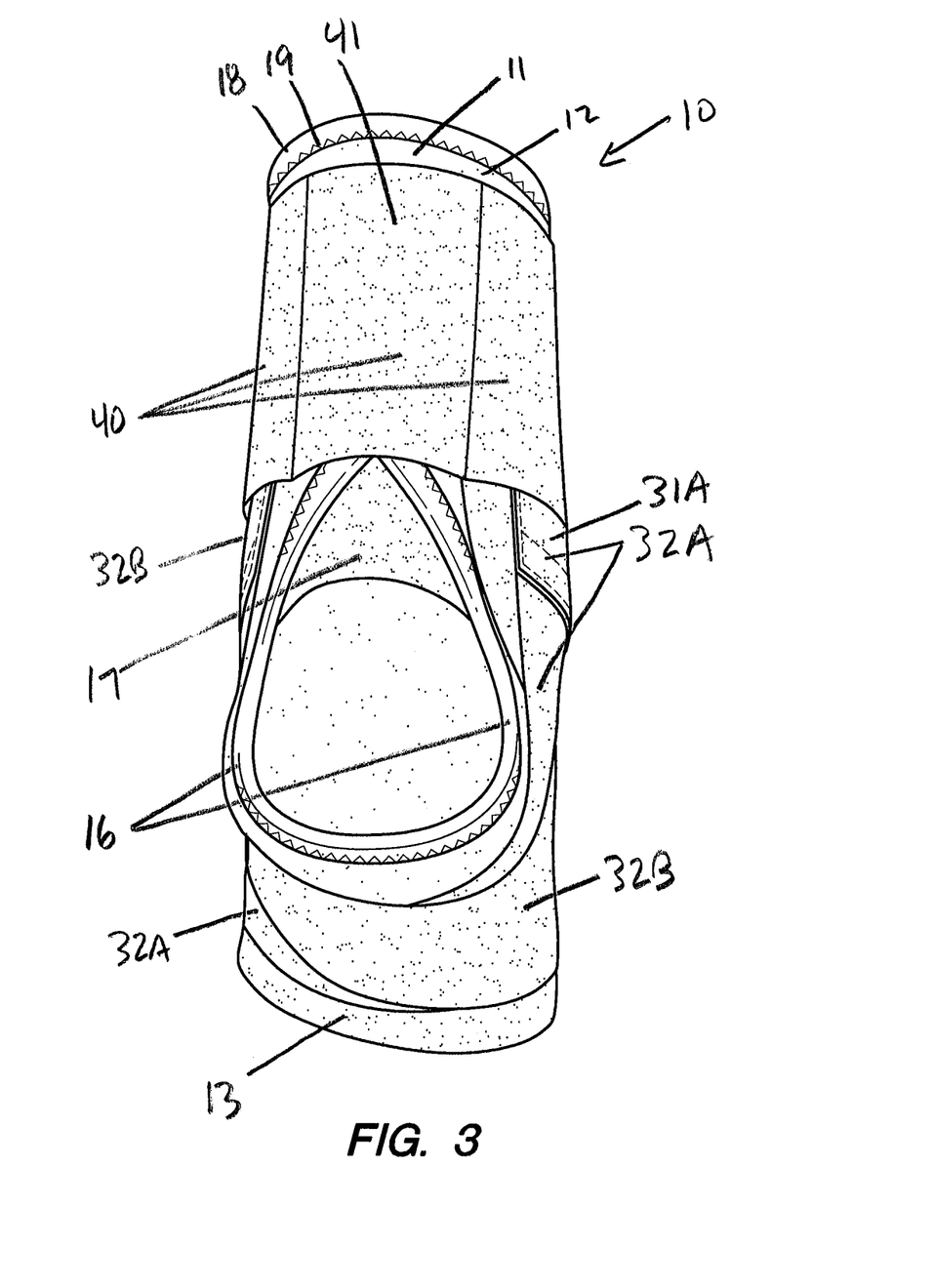
FIG. 3 is a rear view of the ankle brace of FIG. 1.

The ankle brace 10 also includes a floating tongue 20. The floating tongue 20 may be formed of a thin foam or fabric material to provide padding, and may have edging 18 secured with stitches 19. The floating tongue preferably includes a band loop 22 for receiving the elastic band 13, and may also include a lace loop 23 for slidably receiving a portion of the laces 15. The floating tongue 20 is not sewn or otherwise attached to the inelastic body portion 12 of the base 11. The floating tongue 20 may optionally be sewn to the elastic band 13, preferably with a single seam 27 positioned underneath the band loop 22 at the center of the tongue 20, as shown in FIG. 1.

Figure 5:
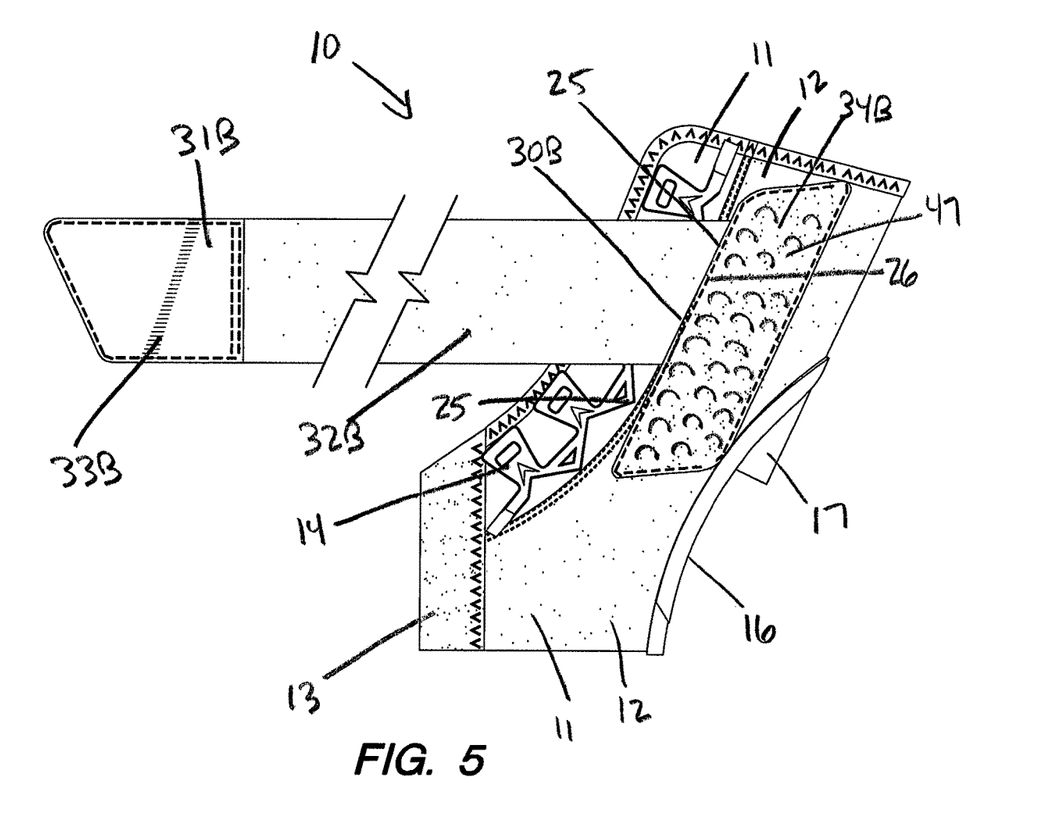
FIG. 5 is a right side view of the ankle brace of FIG. 1, but with the laces and finishing wrap removed, showing how one end of the support strap is sewn to the base of the ankle brace of FIG. 1.
Figure 6A:
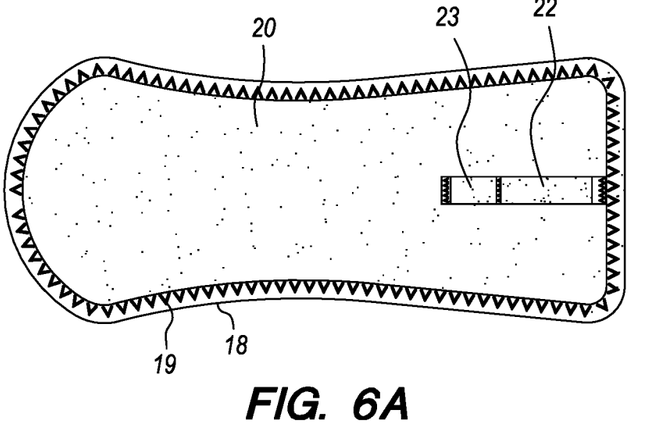
FIGS. 6A and 6B are front and rear views, respectively, of the floating tongue of the ankle brace of FIG. 1.
Figure 6B:
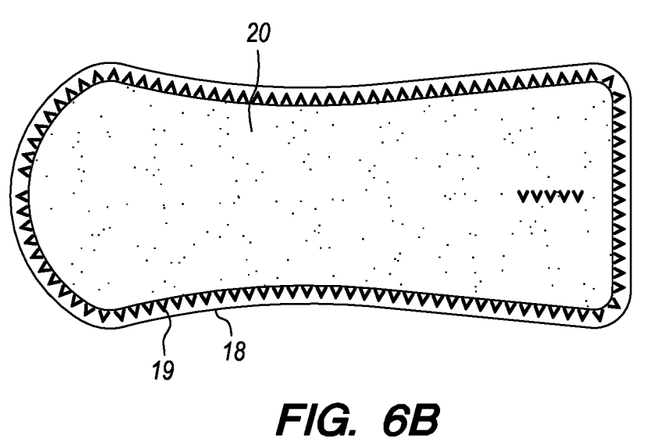
Figure 7A:
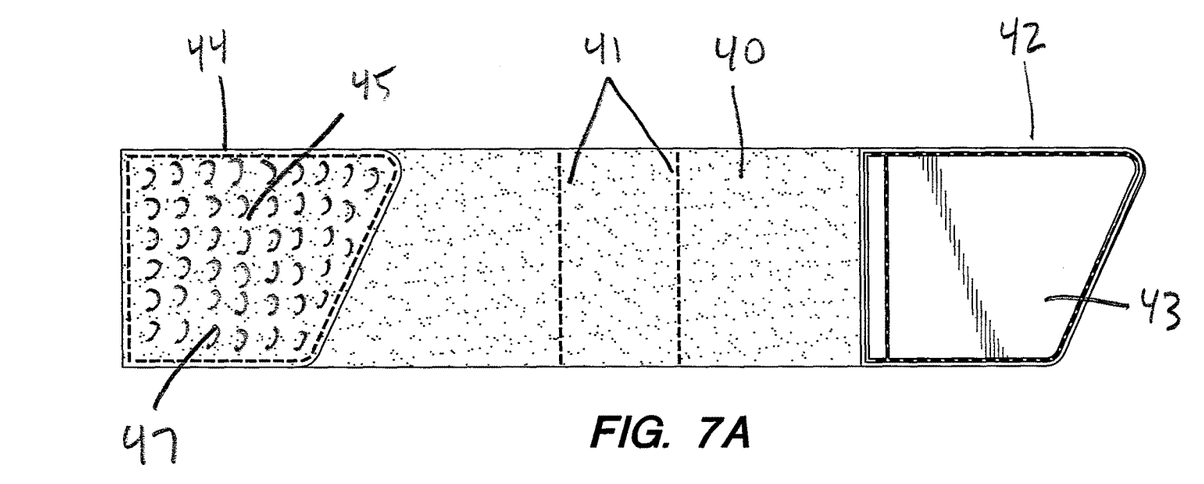
FIGS. 7A and 7B are front and rear views, respectively, of the finishing wrap of the ankle brace of FIG. 1.
Figure 7B:
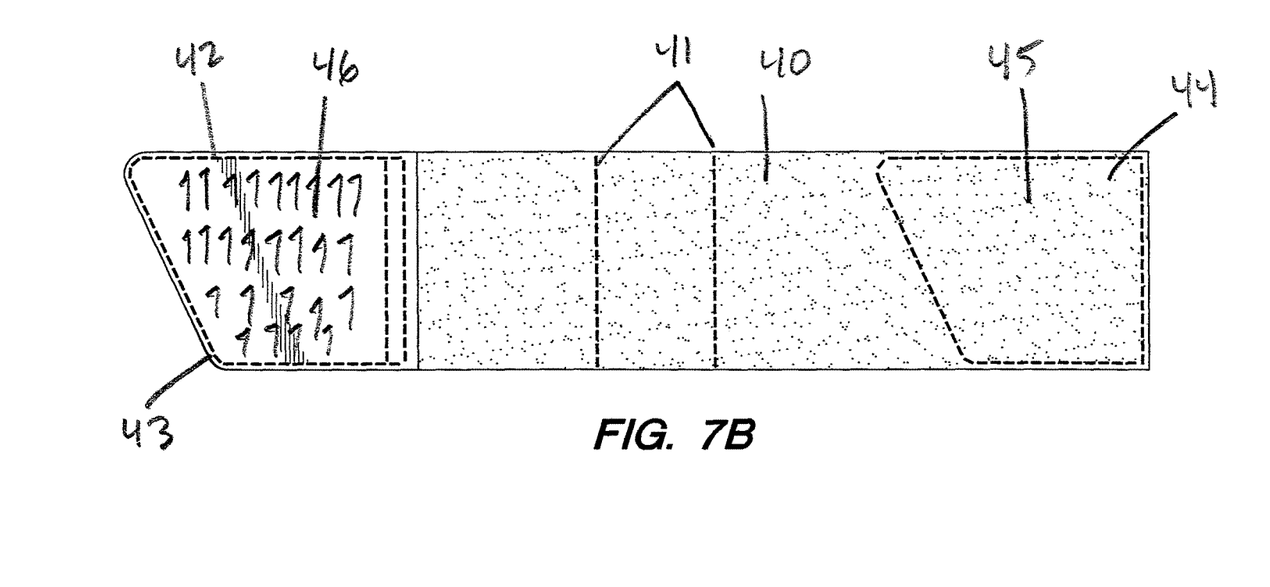
Figure 8A:
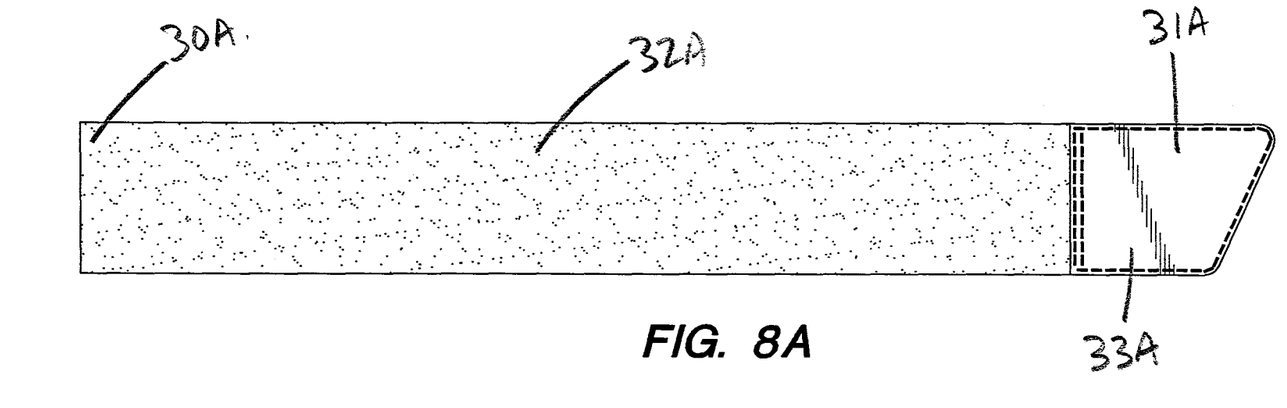
FIGS. 8A and 8B are front and rear views, respectively, of a support strap of the ankle brace of FIG. 1.
Figure 8B:
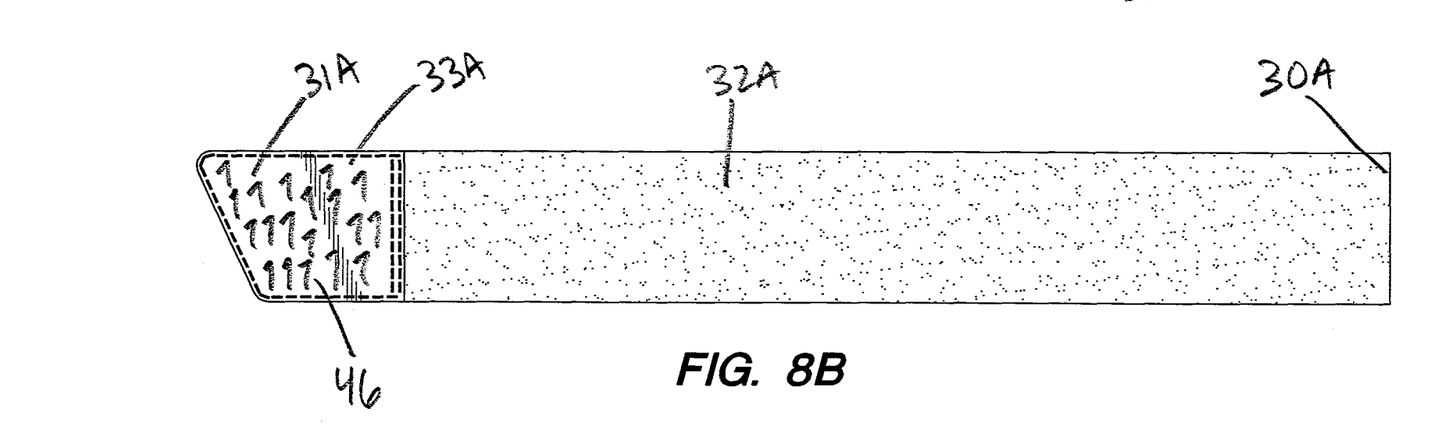

As shown in FIG. 5, the ankle brace 10 also includes a pair of support straps 32A, 32B (one on each side of the base 11) and a pair of fastening patches 34A, 34B bearing loop-type material 47 (one on each side of the base 11). Each support strap 32A, 32B has a fixed end 30A, 30B sewn to the base 11, for example between the rear edge 25 of the eyelet strip and the forward edge 26 of the fastening patch 34A, 34B. Each support strap has a free end 31A, 31B with a fastening tab 33A, 33B bearing hook-type material 46 for detachable attachment to the loop-type material 47 of the fastening patches 34A, 34B.

The ankle brace 10 preferably also includes a finishing wrap having a central portion 41 sewn to the rear of the ankle brace 10 using stitches 19, a first free end 42 bearing a fastening tab 43 bearing hook-type material 46 and a second free end 44 bearing a fastening patch 45 made of loop-type material 47.

The ankle brace 10 is applied to the foot and ankle of a person by first slipping the base 11 over the foot and ankle, then the closure system (e.g. laces 15) is used to secure the base to the foot and ankle, for example by tightening and tying laces 15. Next, (similar to the ankle brace and application procedure shown at col. 2, lines 18-44 in U.S. Pat. No. 5,067,486) the support straps 32A, 32B are each wrapped around the foot with their respective free ends 31A, 31B and fastening tabs 33A, 33B detachably attached to fastening patches 34A, 34B respectively. Finally, the finishing wrap 40 is secured about the ankle with the fastening tab 43 of the first free end 42 detachably attached to the fastening patch 45 of the second free end 44.

The elastic band 13 and floating tongue 20 of the present invention have several advantages. The elastic band 13 holds the brace securely closed to avoid rubbing and hot spots at the forefoot, and in place on the foot to provide more secure support. Compared to a narrower band, the relatively large width (1.0") of the elastic band 13 helps distribute the compression load over more area on the forefoot and keeps the band from "digging in" as a narrower band might do. Compared to a brace having an inelastic base with no elastic forefoot band, the use of the elastic forefoot band 13 allows some extra movement and flexibility in the forefoot while still maintaining adequate restriction and rigidity around the ankle. When lacing the brace up tight to keep the ankle in place, the elastic forefoot band 13 prevents over-tightening around the top of the foot in a way that can irritate the top of the foot. Because the floating tongue is not sewn to the inelastic body portion, the edges of the floating tongue can slide under the inelastic body portion to reduce bunching when the base is tightened about the foot and ankle.

It is understood that the invention is not confined to the embodiments set forth herein as illustrative, but embraces all such forms thereof that come within the scope of the following claims.

What is claimed is:

1. An ankle brace comprising:
   (a) a base having an inelastic body portion formed of inelastic sheet material and having a first body side and a second body side, with a closure system for tightening the base about a foot and an ankle of a person, wherein the body portion extends from an ankle opening to a forefoot opening;
   (b) a first support strap with a first fixed end sewn to the first body side and a first free end bearing a first fastening tab for detachable attachment to a first fastening patch mounted to the first body side, and a second support strap with a second fixed end sewn to the second body side and a second free end bearing a second fastening tab for detachable attachment to a second fastening patch mounted to the second body side;
   (c) an elastic band sewn directly to the forefoot opening of the inelastic body portion whereby the elastic band encircles the forefoot opening; and
   (d) a floating tongue, wherein at least a portion of the floating tongue is positioned between the inelastic body portion and the foot of the person when worn, and wherein the floating tongue is not sewn or otherwise directly attached to the inelastic body portion;
   whereby the tongue can slide under the body portion to reduce bunching when the base is tightened about the foot and ankle;
   wherein the floating tongue includes at its lower end at the forefoot opening a band loop receiving the elastic band, and the elastic band is sewn to the floating tongue underneath the band loop.

2. The ankle brace of claim 1 further comprising a finishing wrap having a central portion sewn to the base, a first free end bearing a fastening tab, and a second free end bearing a fastening patch.

3. The ankle brace of claim 2 wherein the elastic band is between 0.75 inches and 1.5 inches wide.

4. The ankle brace of claim 3 wherein the elastic band is 1.0 inch wide.

5. The ankle brace of claim 1 wherein the elastic band is between 0.75 inches and 1.5 inches wide.

6. The ankle brace of claim 5 wherein the elastic band is 1.0 inch wide.

7. The ankle brace of claim 1 wherein the elastic band is sewn to the floating tongue at a single position.

8. An ankle brace comprising:
   (a) a base having an inelastic body portion formed of inelastic sheet material and having a first body side and a second body side, with a closure system selected from the group (i) shoelaces, (ii) cords, or (iii) straps bearing hook and loop fasteners for tightening the base about a foot and an ankle of a person, wherein the body portion extends from an ankle opening to a forefoot opening;
   (b) a first support strap with a first fixed end sewn to the first body side and a first free end bearing a first fastening tab for detachable attachment to a first fastening patch mounted to the first body side, and a second support strap with a second fixed end sewn to the second body side and a second free end bearing a second fastening tab for detachable attachment to a second fastening patch mounted to the second body side;

(c) an elastic band directly sewn to the forefoot opening of the inelastic body portion whereby the elastic band encircles the forefoot opening; and (d) a floating tongue, wherein a least a portion of the floating tongue is positioned between the inelastic body portion and the foot of the person when worn, and wherein the floating tongue is not sewn or otherwise directly attached to the inelastic body portion;

whereby the tongue can slide under the body portion to reduce bunching when the base is tightened about the foot and ankle;

wherein the floating tongue includes at its lower end at the forefoot opening a band loop receiving the elastic band, and the elastic band is sewn to the floating tongue underneath the band loop.

9. The ankle brace of claim 8 further comprising a finishing wrap having a central portion sewn to the base, a first free end bearing a fastening tab, and a second free end bearing a fastening patch.

10. The ankle brace of claim 9 wherein the elastic band is between 0.75 inches and 1.5 inches wide.

11. The ankle brace of claim 10 wherein the elastic band is 1.0 inch wide.

12. The ankle brace of claim 8 wherein the elastic band is between 0.75 inches and 1.5 inches wide.

13. The ankle brace of claim 12 wherein the elastic band is 1.0 inch wide.

14. The ankle brace of claim 8 wherein the elastic band is sewn to the floating tongue at a single position.

15. An ankle brace comprising:

(a) a base having an inelastic body portion formed of inelastic sheet material with a closure system for tightening the base about a foot and an ankle of a person, wherein the body portion extends from an ankle opening to a forefoot opening;

(b) an elastic band sewn directly to the forefoot opening of the inelastic body portion whereby the elastic band encircles the forefoot opening; and (c) a floating tongue, wherein at least a portion of the floating tongue is positioned between the inelastic body portion and the foot of the person when worn, and wherein the floating tongue is not sewn or otherwise directly attached to the inelastic body portion;

whereby the tongue can slide under the body portion to reduce bunching when the base is tightened about the foot and the ankle;

wherein the floating tongue includes at its lower end at the forefoot opening a band loop receiving the elastic band, and the elastic band is sewn to the floating tongue underneath the band loop.

16. The ankle brace of claim 15 wherein the elastic band is between 0.75 inches and 1.5 inches wide.

17. The ankle brace of claim 16 wherein the elastic band is 1.0 inch wide.

18. The ankle brace of claim 15 wherein the closure system includes an eyelet strip and a shoelace.

19. The ankle brace of claim 18 wherein the floating tongue includes a laces loop, and at least a portion of the shoelace extends through the laces loop.

20. The ankle brace of claim 15 wherein the elastic band is sewn to the floating tongue at a single position.

21. An ankle brace comprising:

(a) a base having an inelastic body portion formed of inelastic sheet material with a closure system selected from the group (i) shoelaces, (ii) cords, or (iii) straps bearing hook and loop fasteners for tightening the base about a foot and an ankle of a person, wherein the body portion extends from an ankle opening to a forefoot opening;

(b) an elastic band sewn directly to the forefoot opening of the inelastic body portion whereby the elastic band encircles the forefoot opening; and (c) a floating tongue, wherein at least a portion of the floating tongue is positioned between the inelastic body portion and the foot of the person when worn, and wherein the floating tongue is not sewn or otherwise directly attached to the inelastic body portion;

whereby the tongue can slide under the body portion to reduce bunching when the base is tightened about the foot and the ankle;

wherein the floating tongue includes at its lower end at the forefoot opening a band loop receiving the elastic band, and the elastic band is sewn to the floating tongue underneath the band loop.

22. The ankle brace of claim 21 wherein the elastic band is between 0.75 inches and 1.5 inches wide.

23. The ankle brace of claim 22 wherein the elastic band is 1.0 inch wide.

24. The ankle brace of claim 21 wherein the closure system includes the shoelaces, and further includes an eyelet strip.

25. The ankle brace of claim 24 wherein the floating tongue further includes a laces loop, and at least a portion of the shoelaces extends through the laces loop.

26. The ankle brace of claim 21 wherein the elastic band is sewn to the floating tongue at a single position.

* * * * *